(12) United States Patent
Pahlck et al.

(10) Patent No.: US 6,245,341 B1
(45) Date of Patent: Jun. 12, 2001

(54) COSMETIC PAN STRUCTURES AND MOLDING METHODS

(75) Inventors: Harold E. Pahlck, Waldwick; Leona Giat Fleissman, Ridgewood, both of NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/131,937

(22) Filed: Aug. 10, 1998

Related U.S. Application Data

(63) Continuation-in-part of application No. 08/853,992, filed on May 9, 1997, now Pat. No. 5,882,662.

(51) Int. Cl.[7] .......................... A61K 7/00; A45D 40/00; A45D 40/24
(52) U.S. Cl. ............................................. 424/401
(58) Field of Search .................. 424/401, 63, 69, 424/64

(56) References Cited

U.S. PATENT DOCUMENTS

| | | |
|---|---|---|
| 1,462,034 | 7/1923 | Finalyson . |
| 1,609,290 | 12/1926 | Broderick . |
| 1,652,755 | 12/1927 | Brodrick . |
| 1,748,964 | 3/1930 | Wacker . |
| 1,985,358 | 12/1934 | Douglas . |
| 2,158,099 | 5/1939 | Aitken ................................. 132/82 |
| 2,573,141 | 10/1951 | Heinrich ................................. 18/55 |
| 3,479,429 | 11/1969 | Morshauser et al. ................. 424/63 |
| 3,851,655 | 12/1974 | Tarro ................................... 132/83 |
| 4,159,028 | 6/1979 | Barker et al. ............................ 141/9 |
| 4,172,113 | 10/1979 | Featherstone et al. ............. 264/319 |
| 4,323,157 | 4/1982 | Idec ..................................... 206/385 |
| 4,337,859 | 7/1982 | Murphy et al. ..................... 206/37 |
| 4,374,796 * | 2/1983 | Ogasawara et al. ................. 264/101 |
| 4,621,935 | 11/1986 | Ssussman ............................ 401/82 |
| 4,650,672 | 3/1987 | Yagita et al. ........................ 424/69 |
| 4,660,608 | 4/1987 | Arai ..................................... 141/12 |
| 4,700,448 | 10/1987 | Parker ................................... 29/434 |
| 4,705,051 | 11/1987 | Bacon et al. ........................ 132/79 |
| 4,743,443 | 5/1988 | Pisani et al. .......................... 424/63 |
| 4,804,538 | 2/1989 | Chen .................................. 424/401 |
| 4,817,686 | 4/1989 | Hatakayama et al. ............. 264/101 |
| 4,884,601 | 12/1989 | Hatakayama et al. ............. 141/701 |
| 4,887,409 | 12/1989 | Israel et al. ........................ 53/436 |
| 4,887,410 | 12/1989 | Gandini .............................. 53/436 |
| 4,962,626 | 10/1990 | Gueret ................................. 53/412 |
| 4,962,627 | 10/1990 | Gueret ................................. 53/412 |
| 4,967,810 | 11/1990 | Arashida ............................. 141/59 |
| 5,073,364 | 12/1991 | Giezendanner et al. ............ 424/63 |
| 5,086,791 | 2/1992 | Ferrari .............................. 132/200 |
| 5,089,256 | 2/1992 | Scheller et al. ...................... 424/63 |
| 5,406,990 | 4/1995 | Haeberli ............................. 141/12 |
| 5,928,658 | 7/1999 | Kishida et al. .................... 424/401 |

FOREIGN PATENT DOCUMENTS

| | | |
|---|---|---|
| 0 191 198A1 | 8/1986 | (EP) . |
| 0 300 519A1 | 1/1989 | (EP) . |
| 0 328 793A1 | 8/1989 | (EP) . |

* cited by examiner

*Primary Examiner*—James M. Spear
(74) *Attorney, Agent, or Firm*—Ohlandt, Greeley, Ruggiero & Perle, LLP

(57) ABSTRACT

A method of forming a cosmetic product by back injection molding is disclosed. The method includes providing a pan having at least one removable wall therein. Each removable wall forms at least two compartments in the pan, with each compartment having apertures therein. The method also includes injecting a first liquid cosmetic through a first of the apertures; injecting a second liquid cosmetic through a second of the apertures, in which the first and second liquid cosmetics may be the same or different; setting the first and second liquid cosmetics without compaction; and removing the at least one removable wall. The present invention also includes pans having breakaway or removable spacer walls, and pans having frame-like structures with open bottom panels. The present invention further includes methods and devices for setting and forming the surfaces of the resulting cosmetics.

17 Claims, 1 Drawing Sheet

COSMETIC PAN STRUCTURES AND MOLDING METHODS

This application is a continuation-in-part of U.S. patent application Ser. No. 08/853,992 for Cosmetic Compositions Containing Smectite Gels, filed May 9, 1997 now U.S. Pat. No. 5,882,662.

The present invention relates generally to molding methods and pan structures used to make cosmetics, preferably by back injection molding processes. More particularly, the present invention relates to methods of molding multi-phase cosmetics in pans, preferably using back injection molding, and the pan structures used therein. The molded cosmetics can include two or more colors of the same cosmetic in a single pan, or can include two different cosmetics in a single pan. Furthermore, they can include two or more surface levels of cosmetic.

BACKGROUND OF THE INVENTION

Back injection molding processes are known in the cosmetic art. Typically, a cosmetic slurry or other flowable base is injected through a hole in the back, or bottom (which may be oriented upwards), of a plastic (or other type) pan structure to form a finished cosmetic product. Alternatively, a cosmetic base can be metered into a pan through its open top. For purposes of this invention, the terms "back injection molding" and "injecting" shall include all of the foregoing, and shall not be limited by the orientation of the pan, the location of the aperture for accepting the cosmetic base, or the force or specific method used to add the cosmetic base to the pan. Moreover, pans can be made of other materials, such as metal, and can have a variety of shapes, such as square, oval or free-form.

Pans are known and marketed that have permanent partitions forming more than one compartment. Different colors or different products can be injection molded or otherwise deposited into the separate compartments to form a multi-phase product. However, it is desirable to have multi-phase products that do not require a permanent internal partition in the pan. Such internal partitions can increase the cost of the pans, and are less aesthetically appealing, particularly when the product is worn away from the partition as it is used up. Moreover, such structures often require double processing and/or blotting of each pan. Packed, compressed multi-phase powder cosmetics are known that include two or more colors or types of compacted cosmetics in direct contact within a single pan.

However, slurried back-injected cosmetics have not been formed in this manner, nor have other cosmetics that are not compacted powders. Accordingly, a need exists for pan structures and molding methods that can be used to form multi-phase cosmetics with back-injection molding techniques and other non-compaction methods.

Similarly, pressed powders are known that have multi-phase surfaces, such as those having decorative embossments or raised areas. However, a need exists for a method to produce such multi-phase surfaces in slurried cosmetic cakes and other non-compacted products.

SUMMARY OF THE INVENTION

It is an object of the present invention to provide a multi-phase cosmetic in a back injection molding process or other non-compaction type process.

It is a further object of the present invention to provide such a multi-phase cosmetic that includes at least two distinct cosmetics in a single pan structure.

It is another object of the present invention to provide a multi-phase cosmetic that includes decorative embossments or raised areas.

It is a further object of the present invention to provide a pan structure for use in back injection of slurried cosmetics that permits formation of multi-phase cosmetics.

Accordingly, the present invention provides a method of forming a cosmetic product by back injection molding. The method includes providing a pan having at least one removable wall therein. Each removable wall forms at least two compartments in the pan, with each compartment having apertures therein. The method also includes injecting a first liquid cosmetic through a first of the apertures; injecting a second liquid cosmetic through a second of the apertures, in which the first and second liquid cosmetics may be the same or different; setting the first and second liquid cosmetics without compaction; and removing the at least one removable wall.

The present invention also includes pans having breakaway or removable spacer walls, and pans having frame-like structures with open bottom panels. The present invention further includes methods and devices for setting and forming the surfaces of the resulting cosmetics.

DESCRIPTION OF THE PREFERRED EMBODIMENTS

The present invention discloses improved methods of forming pan-based cosmetics via back injection molding or other molding methods. A preferred example of the back injection molding processes that may be used in conjunction with the present invention can be found in U.S. Pat. No. 4,967,810 to Arashida, the substance of which is incorporated herein by reference. These methods preferably employ the improved cosmetic formulations disclosed in copending application Ser. No. 08/853,992 for Cosmetic Compositions Containing Smectite Gels, filed May 9, 1997 U.S. Pat. No. 5,882,662, or Ser. No. 09/001,392 for a Back Injection Molding Process, filed Dec. 31, 1997. The disclosures of those applications are incorporated herein by reference. Most preferably, the heat-set polar smectite gels of the former application are used in the methods and structures of the present invention. These gels are formed from polar solvents combined with organophilic smectite clays. This mixture can be formed at ambient temperatures, and without the use of high shear. Moreover, the resulting slurry can be gelled and given structure by the subsequent application of heat to the system.

Figure 1:
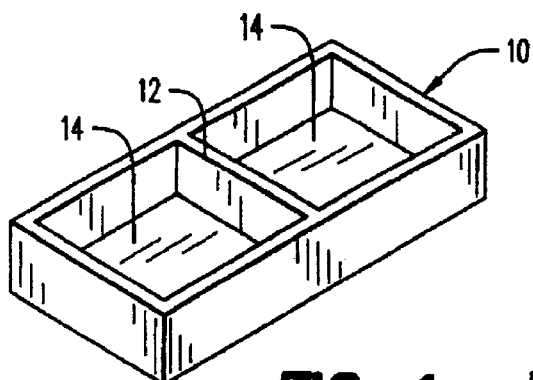
FIG. 1 is a perspective view of a preferred pan structure according to the present invention, the pan having a breakaway separating wall between compartments.

In a first embodiment, it has been discovered that the liquid cosmetic slurry can be back injected into, or otherwise deposited in, a cosmetic pan as shown in FIG. 1, and referred to generally by reference numeral 10. This pan 10 has a break-away separating wall or walls 12. The break-away separating wall 12 is formed integral with the pan 10, or is affixed to the pan in a subsequent step, to form two or more separate compartments 14 for receiving the cosmetic. Wall 12 is capable of separating from the pan structure after the compartments 14 have been filled and the cosmetics therein have set up (e.g., by heat setting or solvent extraction or evaporation). Preferably, the break-away separating wall 12 is removable by means of light mechanical effort. It is preferred that the wall can be simply pulled up and out of the cosmetic. If the wall must be bent or otherwise angled away from the vertical along its line of attachment, the set-up cosmetics may be marred so as to be unacceptable to the consumer without additional corrective steps. Structurally, the break-away separating wall is preferably affixed to the pan via adhesives, gels (including the preferred smectite gels discussed above), waxes or integral perforations formed during molding. The separating wall or walls can be straight, curved or angled, and can define any shape and any number of compartments.

Figure 2:
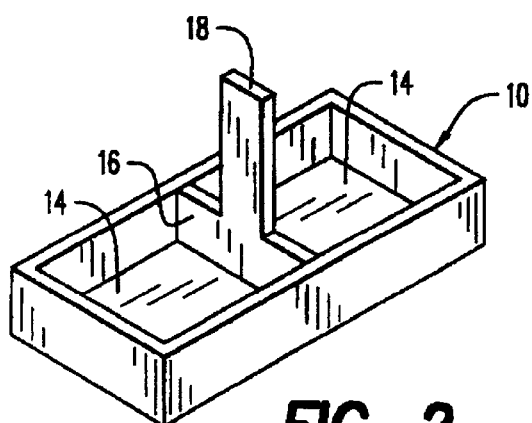
FIG. 2 is a perspective view of another preferred pan structure according to the present invention, the pan being used in conjunction with a removable spacer wall.

In a second embodiment shown in FIG. 2, a spacer wall 16 can be used that is structurally separate from the pan structure. This spacer wall 16 can be hand-held via handle 18, or can be mounted on a separate, movable support structure (not shown). For example, spacer wall 16 can be integrated with or attached to back injection machinery components, such as the element that typically descends onto the filled pan to create a vacuum and press the surface of the cosmetic product. Once the cosmetic slurries are placed in the compartments 14 formed by spacer wall or walls 16, and the slurries are set (e.g., by heat setting or solvent extraction or evaporation), the spacer wall can be removed from the pan. Spacer wall 16 is typically a thin wall, as shown in FIG. 2, but it can also be sufficiently wide to act as a space-saver. When removed, it leaves a vacant area into which another product (e.g., of a different color or a different composition) can be pumped. Thus, this type of spacer wall can be placed into the pan from above during the first filling to maintain a void. This spacer wall would then be lifted once the cosmetic was filled and set. Cosmetic material could then be pumped into any remaining open areas through the hole or holes in the bottom of the pan. For purposes of this invention, the term "spacer wall" shall include substantially flat walls, as well as wider three-dimensional spacing devices for preventing a first pumped product from entering a specific area.

In both of the foregoing embodiments, a heat-swellable, cold flowing cosmetic, such as the polar smectite gel discussed above, is highly preferred for use with the spacer walls and break-away separating walls. These types of cosmetics are preferred, in part, because they do not shrink like a typical wax system can. When such walls are removed from the pans, the set or partially set cosmetics are capable of filling the gap left by the wall or spacer. No additional injection or application of cosmetic slurry is needed to fill the gap. Mechanical agitation of the pan (e.g., tapping) or subsequent application of heat can be used to facilitate the gap-filling process. Otherwise, the gap left behind would be aesthetically undesirable, and could serve to destabilize the product during transport or use.

Consequently, these spacers or walls are preferably used with cold-flowing, heat set gels, or other compositions that are easily rendered slightly malleable after setting. Nonetheless, it is possible, although less preferred, to fill the gap left by the removed wall with a subsequent application of cosmetic material. The methods of the present invention enable the creation of clean, sharp lines of demarcation between adjacent cosmetics.

Moreover, unlike traditional compressed powders, these preferred cosmetics do not require an additional compression phase. Accordingly, the methods of the present invention reduce manufacturing time and expense, and eliminate a high force compression step, which can contribute to product breakage and an elevated reject rate. High force compaction of powder-based cosmetics, which is known in the prior art, is differentiated herein from blotting or other light surface pressure (e.g., surface texturing) applications that are optionally used with the methods and pan structures of the present invention. The latter steps are not the source of the mechanical integrity of the resulting cosmetic product. On the other hand, without compaction, traditional powder-based cosmetics do not form a solid cake, but remain an easily disrupted aggregation of particles.

Figure 3:
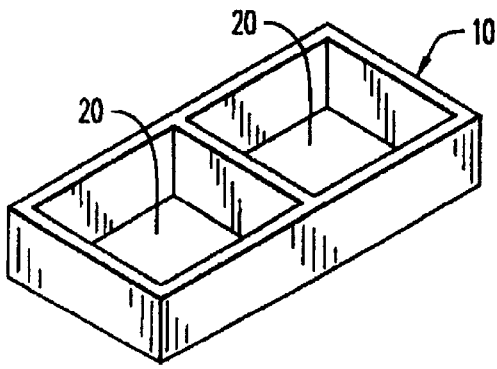
FIG. 3 is a perspective view of another preferred pan structure according to the present invention, this pan being essentially a frame.

A further embodiment of the present invention is shown in FIG. 3. A cosmetic pan 10 for use in molding processes, preferably back injection molding processes, has substantially the entire bottom 20 or back of the pan 10 open. In contrast to typical cosmetic pans in which the bottom is enclosed or has only a small aperture for injection molding, this embodiment discloses a pan structure that is essentially an open frame, having sides only, and optionally, internal partitions.

This open pan structure can also be used with the break-away separating walls or the removable spacer walls disclosed above. This pan structure is simpler and less expensive to make, and requires less accurate alignment, than typical pans. This structure is also preferably used with a somewhat viscous slurry or pre-gelled composition that is less likely to leak out of the frame. Alternatively, this pan is preferably compressed tightly against a support when being filled, to prevent such leakage.

Figure 4:
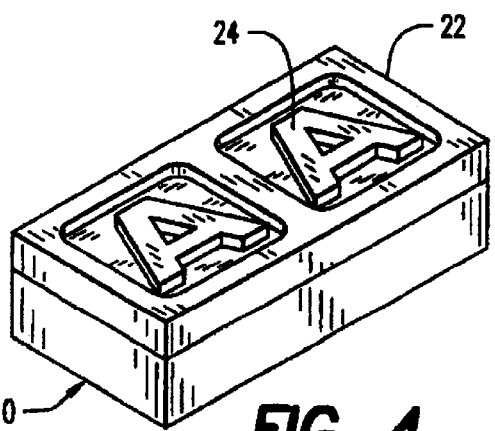
FIG. 4 is a perspective view of the pan of FIG. 3 being used in conjunction with a pan cover.

Another embodiment of the present invention is shown in FIG. 4. A heated pan cover 22 can be used to form raised or depressed designs on the top surface of the cosmetic. Before the cosmetic is back injected, or after it is otherwise added to the pan 10, a three-dimensional heated cover 22 is placed atop the pan. As the cosmetic sets, the cosmetic will take on the shape 24 or shapes molded or otherwise formed in the cover. The heat supplied by the cover 22 permits the formation of sharper, more precise patterns. Moreover, the heat generated by the cover can accelerate the solidification of heat-set cosmetics such as the smectite gels discussed above. The cover 22 can be removed during manufacture (e.g., for reuse) or by the ultimate consumer, revealing a cosmetic cake having an embossed or debossed appearance. As such, the heat source may be integral with or separate from the cover 22. The cover is preferably vented with apertures (not shown), which apertures are used in solvent and air evacuation during back injection molding. It is also envisioned that the cover could include movable sections that can be elevated or dropped relative to one another to produce special visual effects. Once the cover is removed, a separate injection or application of cosmetic product can be used to fill the areas left recessed by the cover to produce different visual effects.

Figure 5:
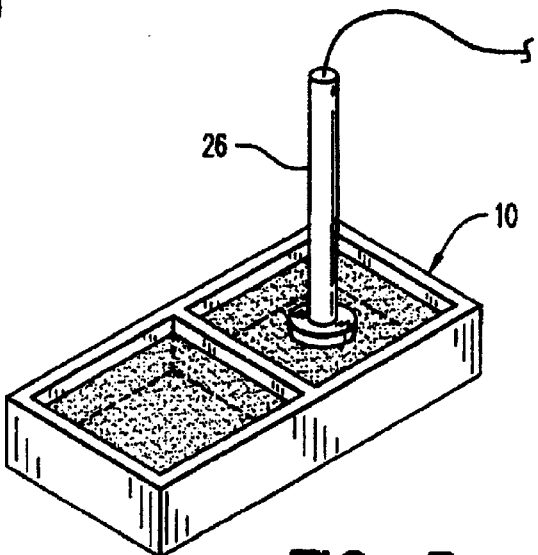
FIG. 5 is a perspective view of the pan of FIG. 3 being used in conjunction with a heated stamp.

In a related vein, the surface of the cosmetic can be embellished by use of a heated stamp 26 as shown in FIG. 5. The heated stamp 26 can be used to form a design on the surface, while simultaneously speeding the heat-setting process (e.g. with the polar smectite gels discussed above). The heated stamp 26 can be applied to the pre-gelled composition and held in place until gelling is complete. The heated stamp 26 can also be applied when preliminary gelling is completed, to aid final gelling and to add dimension to the surface of the cosmetic. For purposes of the present invention, this heated stamp 26 can be any heated element capable of contacting the cosmetic and providing heat to the cosmetic at an acceptable level without burning, scorching or otherwise damaging the cosmetic. Accordingly, the heated cover 22 can be considered an embodiment of the heated stamp 26.

It will be obvious to one of ordinary skill in the art that the foregoing description and drawings are merely illustrative of certain preferred embodiments of the present invention, and that various obvious modifications can be made to these embodiments in accordance with the spirit and scope of the appended claims.

What is claimed is:

1. A method of forming a cosmetic product by back injection molding, comprising:

providing a pan having at least one removable wall therein, said wall forming at least two compartments in said pan, each of said at least two compartments having an aperture therein;

injecting a first cosmetic into a first of said compartments through said aperture therein;

injecting a second cosmetic into a second of said compartments through said aperture therein;

setting said first and second cosmetics without compaction; and removing said at least one removable wall from the pan.

2. The method of claim 1, wherein said removable wall is not affixed to said pan prior to removal.

3. The method of claim 1, wherein said removable wall is a break-away wall that is temporarily affixed to said pan prior to removal.

4. The method of claim 1, wherein at least one of said apertures is substantially the size of a bottom of said compartment in which said aperture is located such that said compartment is substantially a bottomless frame.

5. The method of claim 1, further comprising the step of applying a heated cover to said pan prior to injecting the first and second cosmetics, thus causing at least one of said first and second cosmetics to take on a contour of said heated cover when said first and second cosmetics are set.

6. The method of claim 5, wherein said contour of said cover is three-dimensional, thus producing a raised or depressed design on a top surface of at least one of said first and second cosmetics when said first and second cosmetics are set.

7. The method of claim 1, further comprising the step of contacting at least one of said first and second cosmetics with a heated stamp.

8. The method of claim 7, wherein said step of contacting at least one of said first and second cosmetics with a heated stamp occurs prior to said setting.

9. The method of claim 7, wherein said step of contacting at least one of said first and second cosmetics with a heated stamp occurs prior to said setting and continues until said setting is substantially complete.

10. The method of claim 7, wherein said heated stamp produces a pattern on a surface of at least one of said first and second cosmetics.

11. The method of claim 1, wherein said first and second cosmetics are the same.

12. The method of claim 1, wherein said first and second cosmetics are different.

13. A method of heat-setting and shaping a heat-settable cosmetic composition, comprising applying a heated stamp to said composition before said composition is set.

14. A method of forming a cosmetic product in a pan by back injection molding, comprising:

applying a heated cover to said pan;

injecting a cosmetic into said pan;

setting said cosmetic without compaction;

thus causing said cosmetic to take on a contour of said heated cover when said cosmetic is set.

15. A pan for holding a molded cosmetic composition, said pan comprising a breakaway separating wall releasably affixed by an attachment to said pan and forming at least two compartments in said pan.

16. The pan of claim 15, wherein said break-away separating wall is affixed to said pan by an attachment selected from the group consisting of adhesives, gels, waxes and integral perforations.

17. The method of claim 14, wherein said contour of said heated cover is three-dimensional, thus producing a raised or depressed design on a top surface of said cosmetic when said cosmetic is set.

* * * * *